United States Patent
Hasegawa et al.

(10) Patent No.: US 6,692,474 B1
(45) Date of Patent: Feb. 17, 2004

(54) RECOVERY INSTRUMENT

(75) Inventors: Itaru Hasegawa, Otaru (JP); Minoru Shibata, Akita (JP); Haruhiko Masuda, Akita (JP); Shiro Agehama, Akita (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 0 days.

(21) Appl. No.: 09/787,115

(22) PCT Filed: Jul. 19, 1999

(86) PCT No.: PCT/JP99/03878

§ 371 (c)(1),
(2), (4) Date: May 3, 2001

(87) PCT Pub. No.: WO01/05310

PCT Pub. Date: Jan. 25, 2001

(51) Int. Cl.⁷ .............................................. A61M 31/00
(52) U.S. Cl. ...................................... 604/276; 604/276
(58) Field of Search .......................... 604/264, 5, 6.09, 604/126, 276, 190, 275, 252, 333, 406

(56) References Cited

U.S. PATENT DOCUMENTS

| | | | |
|---|---|---|---|
| 3,939,835 A | 2/1976 | Bridgman | 128/276 |
| 4,639,243 A | * 1/1987 | Schmidt et al. | 604/6 |
| 5,346,469 A | 9/1994 | Ikeda et al. | 604/22 |
| 5,665,094 A | 9/1997 | Goldenberg | |
| 5,807,353 A | 9/1998 | Schmitz | |

FOREIGN PATENT DOCUMENTS

| | | |
|---|---|---|
| FR | 690.847 | 9/1930 |
| JP | 45-7975 | 4/1970 |
| JP | 61-14008 | 1/1986 |
| JP | 64-83227 | 3/1989 |
| JP | 2-109612 | 9/1990 |
| JP | 2-310151 | 12/1990 |
| JP | 3-47222 | 2/1991 |
| JP | 8-266546 | 10/1996 |
| JP | 9-276281 | 10/1997 |
| WO | WO 95/17912 | 7/1995 |

OTHER PUBLICATIONS

Supplementary European Search Report, dated Mar. 20, 2003, issued by the European Patent Office, for European Patent Application No. 99929898.7 (3 pages).

* cited by examiner

Primary Examiner—Manuel Mendez
(74) Attorney, Agent, or Firm—Smith, Gambrell & Russell, LLP

(57) ABSTRACT

A medical instrument, or collection instrument, for collecting foreign material, such as calculuses and clips that have fallen in the abdominal cavity, is disclosed. The collection instrument includes a tube (1) that is hollow in the longitudinal direction and a collection bag (2) arranged at one end of the tube (1). The collection bag includes a barrier member having a fluid passage characteristic.

10 Claims, 1 Drawing Sheet

RECOVERY INSTRUMENT

BACKGROUND OF THE INVENTION

The present invention relates to a collection instrument, and more particularly, to a collection instrument employed in endoscopic surgeries using pneumoperitoneum gas, such as laparoscopic surgeries, to easily collect through simple manipulations bodily substances, such as a calculuses that fall in an operation region or bodily substances such as a calculuses exposed from an end region or an incised region of a gallbladder duct or common bile duct.

Presently, many facilities perform laparoscopic cholecystectomy on benign gallbladder patients. During laparoscopic cholecystectomy, a region near the navel is punctured by a pneumoperitoneum needle or slightly incises to insert a trocar, and the pneumoperitoneum needle or the trocar insufflates carbonic acid gas into the abdominal cavity to perform pneumoperitoneum. Then, the abdominal wall is punctured by a plurality of trocars, and endoscopes or various treatment instruments are inserted in to the abdominal cavity to perform laparoscopic cholecystectomy.

Enucleation is performed after confirming the gallbladder, by ablating the gallbladder duct, ligating the ablated gallbladder with a clip, and finally dissecting the gallbladdeer in the ligated region. The dissected gallbladder is collected through the abdominal wall. However, there may be cases in which the gallbladder is ruptured or the clip becomes disengaged. Since the gallbladder often contains a calculus, the calculus may fall into the abdominal cavity and be fragmented if the gall bladder is ruptured or if the clipping of the dissected region is insufficient. Further, as mentioned above, the clip may fall into the abdominal cavity when clipping the gallbladder duct prior to dissection.

If a calculus or clip falls into the abdominal cavity, each dropped piece must be extracted using forceps. However, this takes time and is a great burden on the patient. Further, since the surgery requires general anesthesia, the burden on the patient increases as the anesthetic time increases.

In addition to cholecystectomy, the same problem occurs when performing enucleation of the womb or the ovary or when performing partial excision of the lung.

The inventors of the present application have taken notice that the pneumoperitoneum pressure is higher than the atmospheric pressure by 6 to 12 mmHg and have conceived an instrument for easily collecting calculuses and clips, which fall into the abdominal cavity, and bodily substances, such as a calculus, that is exposed from an end region or a incised region of a gallbladder duct or common bile duct. The inventors have then studied endoscopic surgeries using pneumoperitoneum gas from many aspects to make the present invention.

SUMMARY OF THE INVENTION

It is an object of the present invention to provide a medical instrument that easily and quickly collects calculuses and clips, which fall into an abdominal cavity undergoing pneumoperitoneum, and foreign objects, such as a calculus or a clip, that are exposed from an end region or a incised region of a gallbladder duct or common bile duct.

A collection of instrument according to the present invention includes a tube that is hollow in the longitudinal direction and a collection bag arranged at one end of the tube. The collection bag is characterized by a barrier member having a fluid passage characteristic.

BEST MODE FOR CARRYING OUT THE INVENTION

Figure 1A:
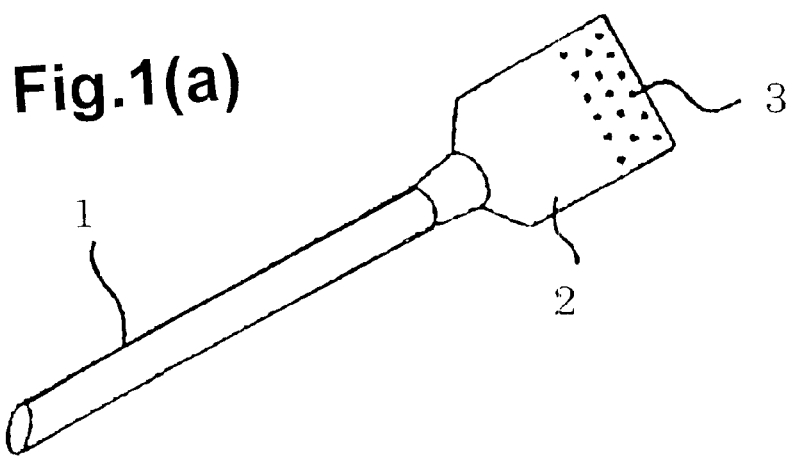
FIG. 1(a) is a perspective view showing a collection instrument according to a first embodiment of the present invention.
Figure 1B:
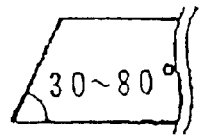
FIG. 1(b) is an enlarged side view of a distal portion of FIG. 1(a).
Figure 2A:
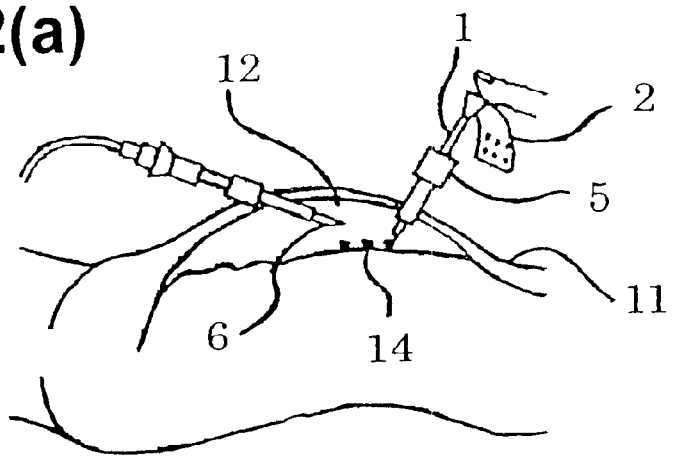
FIG. 2(a) is a diagram illustrating how the collection instrument according to the embodiment of the present invention is used.
Figure 2B:
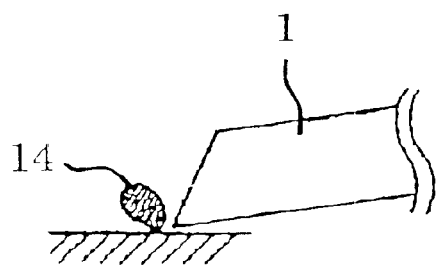
FIG. 2(b) is a diagram showing how the distal portion of the collection instrument is contacted with a calculus.

The present invention will now be described with reference to the drawings. FIG. 1(a) shows a collection instrument according to an embodiment of the present invention. FIG. 1(b) is an enlarged side view of a distal portion of the collection instrument of FIG. 1(a). FIG. 2(a) is a diagram illustrating how the collection instrument of the present invention is used. FIG. 2(b) is a diagram showing how the distal portion of the collection instrument is contacted with a calculus.

In the present invention, it is preferred that a tube (1), which is inserted into an abdominal cavity (12) through a trocar (5) arranged at an abdominal wall (11), be made of a material that has a superior squeezing characteristic and bends little. Normally, the tube (1) may be formed in a straight pipe-like manner. However, the tube (1) may also be curved slightly to handle cases in which a calculus is located at a location difficult to reach, such as at a lower surface of the hepatic diaphragm. Further, it is especially preferable that the tube (1) be made of a material which surface has a relatively small friction coefficient to enable trocar insertion and the passage of calculuses, clips, or the like. Such materials include, for example, metals such as stainless steel and titanium, and carbon fiber, Teflon, polyethylene, polypropylene, nylon, polyester, polyacetal, or the like. However, the present invention is not limited to these materials.

In the present invention, an appropriate barrier member is selected as a collection bag (2). The barrier member must prohibit the passage of the object that is to be collected and allow the passage of fluids. A value indicating the fluid passage characteristic (fluid passage rate) is at least 1 ml/sec./mmHg. A fluid passage rate that is less than 1 ml/sec./mmHg is not preferred since objects cannot be moved because the required fluid movement for moving objects is not produced. A barrier member satisfying these conditions may be used as the collection bag. For example, in the embodiment shown in FIG. 1, a large amount of small pores (3), the diameters of which are about one millimeter, is provided at the bottom portion of the collection bag (2) to satisfy these two conditions. If a collection bag made from a nonwoven fabric is used, objects having diameters that are one millimeter or less can be caught.

The joining of the tube (1) and the collection bag (2) is not restricted, and various means may be employed, such as fastening with an adhesive or a band.

To efficiently move a fallen calculus, the distal portion of the tube (2) is formed so that the angle of the plane defined by the distal opening in the longitudinal direction, or the angle shown in FIG. 1(b) is 30 to 80°. It is not preferable that the tube distal portion angle be less than 30° since the distal end becomes sharp and may thus damage tissues when inserted into the abdominal cavity. It is also not preferable that the tube be greater than 80° since this would draw the tissues about the calculuses into the tube (1) and close the inlet of the tube (1).

A method for using the collection instrument according to the present invention of FIG. 2 will now be described to clarify the advantages of the present invention. The present invention uses pneumoperitoneum pressure, which is higher than the almospheric pressure by 6 to 12mmHg as mentioned above, as an energy source for moving objects.

The tube (1) is first inserted into the abdominal cavity (12) through the trocar (5). When doing so, the surgeon's fingers must continue to press one end (hereafter referred to as basal portion) of the tube from above the collection bag (2). Under laparoscopic observation, the distal end of the tube (1) is then moved toward a fallen calculus (14). As shown in FIG. 2, in this state, the opened surface at the distal end opening of the tube (1), which has an angle of 30 to 80°, is faced upward. By arranging the distal end of the tube (1) to pick up the calculus (14) and momentarily releasing the fingers from the basal portion, the calculus (14) is instantaneously drawn into the tube (1) and collected in the collection bag (2). If there is more than one calculus that has fallen, the same manipulation is repeated to collect the calculuses.

The opening at the distal end of the tube (1) should not be faced downward. If the fallen calculus (14) is collected with the tube (1) faced downward, tissues may be drawn into the tube (1) thereby closing the opening.

This phenomenon occurs because of the pressure difference between the outside and the inside of the abdominal cavity. In other words, since the pressure inside the abdominal cavity (12) is higher than the pressure outside the abdominal cavity, when the distal portion of the tube (1) is released from the state shown in FIG. 2, the objects in the abdominal cavity are forced to the abdominal cavity exterior, which pressure is lower. This state can easily be understood when comparing it to a phenomenon in which, when a hole is formed in the body of a flying spaceship or airplane, objects inside the body are sucked out of the body through the hole.

The collection instrument according to the present invention uses the pressure difference effectively to collect calculuses and clips that fall into or are exposed in the abdominal cavity. Thus, in comparison with collection using forceps, the collection instrument completes collection within a short period of time.

The present invention enables the collection of calculuses and clips that fall into or are exposed in the abdominal cavity and is very effective for use as a medical instrument that decreases the burden on the surgeon and the patient.

In addition to cholecystectomy, the present invention may be used in all kinds of surgeries using pneumoperitoneum gas, such as during the enuceration of the womb or the ovary. Further, in addition to calculuses and clips, the collected objects may be dissected tissues, or the like. The collection instrument is very effective for endoscopic surgeries that use pneumoperitoneum gas.

What is claimed is:

1. A medical collection instrument comprising:
   a tube that is hollow in the longitudinal direction; and
   a collection bag arranged at one end of the tube and made of a barrier member having a fluid passage characteristic.

2. The collection instrument according to claim 1, wherein an angle of a plane defined at a distal end opening of the tube relative to the longitudinal direction of the tube is about 30 degrees to about 80 degrees.

3. The collection instrument of claim 1, wherein an angle of a plane defined at a distal end opening of the tube relative to the longitudinal direction of the tube is about 30 degrees to about 80 degrees.

4. The collection instrument of claim 1, wherein the collection bag is made of a non-woven fabric.

5. A medical collection instrument comprising:
   a generally straight tube formed of a squeezable material; and
   a collection bag attached to a proximal end of the tube, wherein the bag prohibits the passage of objects and allows the passage of fluids, a value of the fluid passage being about 1 ml/sec/mmHg, and wherein a distal end of the tube is formed so that an angle of a plane defined at a distal end opening of the tube relative to the longitudinal direction of the tube is about 30 degrees to about 80 degrees.

6. The collection instrument of claim 5, wherein the tube is curved slightly.

7. The collection instrument of claim 5, wherein the tube material has a low coefficient of friction.

8. The collection instrument of claim 5, wherein the collection bag is made of a non-woven fabric.

9. The method of claim 5, wherein the pressurizing step includes setting the pressure of the abdominal cavity higher than the atmospheric pressure by 6 to 12 mmHg.

10. A method for using a medical collecting instrument for collecting a fallen object in an abdominal cavity, wherein the collecting instrument includes a tube and a collection bag attached to a proximal end of the tube, wherein a distal end of the tube is formed so that an angle of a plane defined at a distal end opening relative to the longitudinal direction of the tube is about 30 degrees to about 80 degrees, and the collection bag is made of a barrier member having a fluid passage characteristic, the method comprising the steps of:
   pressurizing the abdominal cavity at a pressure higher than the atmospheric pressure;
   closing a proximal end opening of the tube by a finger from above the collection bag;
   inserting the tube into the abdominal cavity through a trocar while continuing to close the distal end opening;
   moving the distal end of the tube toward the fallen object under laparoscopic observation;
   facing the distal end opening upward; and
   releasing the finger to open the proximal end opening so that the fallen object is drawn into the collection bag through the tube due to the difference between the pressure of the abdominal cavity and the atmospheric pressure.

* * * * *